(12) United States Patent
Quan

(10) Patent No.: US 11,141,362 B2
(45) Date of Patent: *Oct. 12, 2021

(54) NANOEMULSIONS COMPRISING GLYCEROL IN AQUEOUS PHASE

(71) Applicant: Conopco, Inc., Englewood Cliffs, NJ (US)

(72) Inventor: Congling Quan, Woodbridge, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/480,752

(22) PCT Filed: Jan. 4, 2018

(86) PCT No.: PCT/EP2018/050215
§ 371 (c)(1),
(2) Date: Jul. 25, 2019

(87) PCT Pub. No.: WO2018/145828
PCT Pub. Date: Aug. 16, 2018

(65) Prior Publication Data
US 2019/0388308 A1    Dec. 26, 2019

(30) Foreign Application Priority Data

Feb. 8, 2017 (EP) .................................. 17155138

(51) Int. Cl.
| | |
|---|---|
| *A61K 8/44* | (2006.01) |
| *A61Q 19/10* | (2006.01) |
| *A61K 8/06* | (2006.01) |
| *A61K 8/31* | (2006.01) |
| *A61K 8/34* | (2006.01) |
| *A61K 8/36* | (2006.01) |
| *A61K 8/37* | (2006.01) |

(52) U.S. Cl.
CPC .................. *A61K 8/06* (2013.01); *A61K 8/31* (2013.01); *A61K 8/345* (2013.01); *A61K 8/361* (2013.01); *A61K 8/375* (2013.01); *A61K 8/44* (2013.01); *A61Q 19/10* (2013.01); *A61K 2800/21* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,500,152 A | 3/1996 | Helliwell | |
| 5,854,293 A | 12/1998 | Glenn, Jr. | |
| 6,066,608 A | 5/2000 | Glenn, Jr. | |
| 6,541,018 B1 * | 4/2003 | Simonnet | A61K 9/1075 424/401 |
| 8,772,212 B2 | 7/2014 | Restrepo et al. | |
| 8,834,903 B2 | 9/2014 | Simonnet et al. | |
| 2003/0077299 A1 | 4/2003 | Iwai et al. | |
| 2017/0087064 A1 * | 3/2017 | Ikeda | A61K 8/06 |

FOREIGN PATENT DOCUMENTS

EP         105287235         2/2016

OTHER PUBLICATIONS

IPRP1 in PCTEP2018050215; Aug. 13, 2019.
Search Report in EP17155138; dated Apr. 25, 2017. pp. 1-5.
Search Report and Written Opinion in PCTEP2018050215; dated Feb. 28, 2018; pp. 6-17.

* cited by examiner

*Primary Examiner* — Celeste A Roney
(74) *Attorney, Agent, or Firm* — Krista A. Kostiew

(57) ABSTRACT

The present invention relates to novel oil-in-water nanoemulsions. The oil phase contains oil selected from the group consisting of triglyceride oil and/or petrolatum as well as C8 to C18 fatty acid; and the aqueous phase contains specific N-acyl derivatives having specific counterions of amino acid salt as emulsifier, glycerol, and water. When (i) there is defined ratio of glycerol to water; (ii) specific counterion for amino acid surfactant and (iii) fatty acid in oil phase. Nanoemulsions are processed in a one-step process yielding droplets of size 20 to 400 nm. In one embodiment, droplets of size 20 to 400 nm can be made using rotor-stator device (in one-step process) and in the absence of pressure based homogenizer. This saves in energy and cost. Compositions prepared according to this processes are also contemplated.

14 Claims, No Drawings

NANOEMULSIONS COMPRISING GLYCEROL IN AQUEOUS PHASE

CROSS REFERENCE TO RELATED APPLICATIONS

The present application is a U.S. National Phase Application under 35 U.S.C. § 371 of International Application No. PCT/EP2018/050215, filed on Jan. 04, 2018, which claims priority to European Patent Application No. 17155138.5, filed on Feb. 08, 2017, the contents of which are incorporated herein in their entireties.

FIELD OF THE INVENTION

The present invention relates to novel oil-in-water (o/w) nanoemulsions wherein the weight ratio of glycerol over water ranges from 3:1 to 1:3 in the aqueous phase. More specifically, the nanoemulsions contain (1) an internal oil phase having triglyceride oils and/or petrolatum and $C_8$ to $C_{18}$ fatty acid; and (2) an external aqueous phase containing surfactants comprising specific salts of N-acyl derivatives of dicarboxylic amino acids (e.g., potassium and/or trialkanolamine salts of aspartic acid, glutamic acid), specific salts of N-acyl derivatives of monocarboxylic acids (e.g., potassium and/or trialkanolamine salts of glycine, alanine), or mixtures of such derivatives of mono and dicarboxylic amino acids; and wherein the weight ratio of glycerol over water ranges specifically from 3:1 to 1:3 in the aqueous phase. Nanoemulsion droplets ranging from 20 to 400 nanometers (nm) can be prepared using such systems.

It further relates to novel processes wherein nanoemulsions having droplets of 20 to 400 nm are prepared using conventional rotor-stator high shear mixers (based on high-speed rotation of the rotor blades, measured by revolutions per minute, or rpm). Typically, nanoemulsions (other than our specifically defined systems) are not producible without using a homogenizer device applying high pressure (measured by, e.g., pounds per square inch or psi).

BACKGROUND OF THE INVENTION

The invention is concerned with the provision of triglyceride oils and petrolatum (benefit agents delivered from nanoemulsion), preferably in small droplets (e.g., 400 nanometers or less, preferably 20 to 250 nm). The nanoemulsions further provide high deposition of the triglyceride oil and/or petrolatum when being incorporated in personal cleansing compositions. Excellent lather performance of personal cleansing compositions is found when these benefit agents are present in the form of droplets of 400 nanometers or less; triglyceride oil and petrolatum benefit agents tend to depress lather speed and volume when in the form of droplets of a few microns (i.e., much larger than those of the invention).

N-acyl derivatives of both dicarboxylic and monocarboxylic amino acid surfactants of the invention are exceptionally mild surfactants which form the novel nanoemulsions, and which, when the nanoemulsions are incorporated into fully formulated personal liquid cleaners, do not interrupt formation of micellar and/or lamellar structured liquids, nor do they suppress lather. Nanoemulsions comprising oils, fatty acid and amino acid based surfactants are claimed in a co-pending application. The amino acid based surfactants are found in an external aqueous phase. Applicants have now found that combination of (1) glycerol in the external aqueous phase wherein the ratio of glycerol to water is preferably in the range of 3:1 to 1:3, (2) use of highly water soluble triethanolamine (TEA) or potassium salts of the mono- and dicarboxylic amino acid based surfactants in aqueous phase (which tend to be more water soluble than other counterions; sodium salts may be present but are 35% or less of all counterions on the amino acid surfactants while potassium and TEA are 65% and higher), and (3) use of fatty acid in the oil phase allows formation of oil droplets having size of 20 to 400 nm; or 20 to 250; or 20 to 200. In a separate form, applicants have found a process for making these nanoemulsions having droplet size of 20 nm to 400 nm, preferably 20 nm to 250 nm using a conventional rotor-stator mixer. It is remarkable that nanoemulsions of such small particle size can be formed without high pressure homogenization devices and can be done using conventional rotor-stator mixers. This results in saving on energy as well as on expensive equipment, eliminating a significant barrier for wide applications of nanoemulsions in cosmetic industry. Compositions made by the process are also claimed.

Moreover, because glycerol is used in place of water, there is lowered water activity, e.g., from 0.96 to as low as 0.68. This level of water activity is within the ranges to inhibit bacteria growth, and potentially allows use of only fungicide or even no preservatives in nanoemulsions either as an intermediate raw material or as a final product.

Skin moisturizing oils (including triglyceride oils and petrolatum benefit agents noted above) are often delivered from personal cleansing compositions (e.g., shower gels, facial and hand cleansers designed to cleanse and moisturize skin) in the form of large oil drops (e.g., 50 to 200 microns or greater).

U.S. Pat. Nos. 5,854,293 and 6,066,608, both to Glenn, Jr., for example, disclose a moisturizing liquid personal cleansing emulsion with at least 10% lipophilic skin moisturizing agent droplets having a diameter of greater than 200 microns. The reference is not concerned with nanoemulsions.

U.S. Pat. No. 8,772,212 to Restrepo et al. discloses an isotropic cleansing composition containing high level of petrolatum; greater than 50% by volume of the petrolatum particles have a diameter greater than 50, 100, 150 or 200 microns. The reference is not concerned with nanoemulsions.

Compositions containing large oil drops need to be well structured so they can suspend the large droplets (using, for example, stabilizers). U.S. Pat. Nos. 5,854,293 and 6,066,608, for example, utilize stabilizers selected from crystalline, hydroxyl-containing stabilizers, polymeric thickeners, $C_{10}$-$C_{18}$ diesters, amorphous silica or smectite clay. Special blending processes are typically needed to prepare such compositions. For example, compositions must be prepared under low shear to prevent oil droplet size reduction (see U.S. Pat. No. 8,772,212). Although they provide enhanced delivery of benefit agents, these products are generally considered to be less aesthetically appealing to the consumer due to the presence of large oil droplets.

Another method of enhancing the delivery of a benefit agent (e.g., silicone) to the skin, for example, is through the use of cationic hydrophilic polymers such as, for example, hydroxypropyltrimethylammonium derivative of guar gum, sold under the name JAGUAR® C-13-S (see U.S. Pat. No. 5,500,152 to Helliwell). In this reference, silicone oil is a preformed emulsion with oil droplet size ranging from 0.1-1 micron (μm), with a mean particle size of 0.4 μm (there is no mention whether this refers to number average or volume average diameter of droplets). This kind of product tends to be smooth and aesthetically appealing. However, nourishing vegetable oils (triglyceride oils) and highly occlusive skin protectants, such as petrolatum, are typically preferred moisturizers from a cleansing composition.

One challenge facing cleansing compositions that are rich in moisturizing oils is that large amount of oils tend to depress the lather speed and volume.

It is therefore desirable to prepare a personal cleansing composition consisting of triglyceride oils and/or petrolatum nanoemulsion, which is aesthetically appealing, high in deposition of these moisturizing oils, and which maintains high lather performance.

In the subject invention, applicants provide novel nanoemulsions for delivery of triglyceride oils and petrolatum, preferably as small (20 to 400 nanometers, particularly 20 to 250 nanometers, more particularly 20 to 200 nanometers) volume average diameter droplets. Unexpectedly, by using glycerol in the aqueous phase wherein the weight ratio of glycerol over water ranges from 3/1 to 1/3, selecting more water soluble Triethanolamine (TEA) or Potassium salts of mono- and dicarboxylic amino acid based surfactants in aqueous phase, and including fatty acid in oil phase, applicants have found they can prepare nanoemulsions of small droplet size. In another embodiment, the invention discloses a process for preparing the noted nanoemulsions have droplet size of 20 nm to 400 nm, preferably 20 nm to 250 nm using a conventional rotor-stator mixer. The magnitude of droplet reduction, achieved using conventional rotor-stator high shear devices typically used in cosmetic industry, is very surprising. Moreover, the use of expensive, energy intensive homogenizers which are based on pressure feeding through a narrow inlet is thereby avoided. Compositions produced by this process are also claimed by the invention.

A further advantage is that, with the introduction of glycerol, water activity ($a_w$) of the nanoemulsion is significantly lowered, from 0.96 to as low as 0.68. This water activity is within the ranges where bacteria growth is inhibited even without use of additional bactericide. Thus, levels of glycerol contemplated for use in our nanoemulsions potentially allows use of only fungicide (e.g., no bactericide) or even no preservatives at all, where nanoemulsions may either be used as an intermediate raw material or as a final product.

In a co-pending application, applicants claim similar nanoemulsions comprising the salts of N-acyl derivatives of di-carboxylic amino acid (e.g., acylglutamate) and/or monocarboxylic acid (e.g., acylglycinate); or use of specific co-emulsifiers (fatty acid) which enable the use of high salt and high pH liquid forms of both di- and mono-carboxylic amino acid based surfactants. However, there is no disclosure of the benefit of glycerol in the aqueous phase or of claimed glycerol to water ratios. There is further no disclosure of process for making droplet size of 20 to 400 nm, preferably 20 to 250 nm using rotor-stator mixer, i.e., in absence of high pressure homogenizers. There is further no disclosure of minimizing levels of preservative needed (due to lowered water activity).

Both U.S. Pat. Nos. 8,834,903 and 6,541,018 to Simonnet et al. disclose nanoemulsion compositions in which acylglutamate is mentioned as possible surfactant (e.g., U.S. Pat. No. 8,834,903 at column 4, lines 27-31). Glycerol is only mentioned as an optional component as one of several possible glycol additives which can be added to improve transparency (e.g., U.S. Pat. No. 8,834,903 at column 6, lines 34-60 and U.S. Pat. No. 6,541,018 at column 6, lines 5-29). There is also no disclosure of process for making droplets of 20-400 nm in the absence of high pressure homogenizer devices. It is our specific compositions, and ratios of glycerol to water which permits our process of forming small drops using rotor-stator mixers. The criticality of glycerol levels in general, and ratios of glycerol to water is simply not appreciated.

CN105287235A to Lu et al discloses nanoemulsion compositions in which sodium stearoyl glutamate or sodium stearoyl-cocoyl glutamate are used as emulsifier (page 2, paragraph [0017]) and 1 to about 60% of which is water soluble small molecules selected from glycerol, butylene glycol and propylene glycol. There is no disclosure of fatty acid as co-emulsifier (page 2, paragraph [0017]). There is further no disclosure of our process for producing nanoemulsions with droplet size 20 to 400 nm. Our process requires the specific use of glycerol and the glycerol to water ratios claimed.

US 2003/0077299 A1 to Iwai et al. discloses an o/w emulsion in which oil phase comprises a ceramide or fatty acid (page 1, paragraph [0009]). Glycerol is only optional in aqueous phase (e.g. Page 6, example 6 contains no glycerol). There is no disclosure of the specific nanoemulsions, process for making droplets of 20 to 400 nm in the absence of high pressure homogenizer, or of compositions made by the process using conventional rotor-stator mixer.

Sodium salts of acyl glutamate are mentioned in all the above cited references. None teaches the requirement of using predominately (65% or more) triethanolamine (TEA) or potassium counterions of the carboxylic amino acid based surfactants, or that this is needed to use the process of the invention for forming droplets of 20 to 400 nm, preferably 20 to 250 nm.

BRIEF DESCRIPTION OF THE INVENTION

The present invention relates in one form to nanoemulsion compositions comprising:
  a) an internal oil phase comprising (i) 40 to 75% by wt. of total nanoemulsion of an oil selected from the group consisting of triglyceride oil, petrolatum and mixtures thereof, wherein the melting point of the petrolatum is 30 to 60° C.; and (ii) 1.5 to 10% by wt. nanoemulsion of a $C_8$ to $C_{18}$, preferably $C_{10}$ to $C_{14}$ fatty acid (e.g., $C_{12}$ lauric acid); and
  b) an external aqueous phase comprising
    (i) 2 to 12% by wt. (as active) of total nanoemulsion of a surfactant or surfactants which are the salts of N-acyl derivatives of amino acid wherein, preferably, said surfactant or surfactants is selected from the group consisting of
      A. salt of N-acyl derivatives of di-carboxylic amino acid (e.g., acylglutamic acid or acylaspartic acid), wherein greater than 65% (e.g., 65 to 100%, preferably 65 to 90%) of the acyl group has chain length of $C_{14}$ or less;
      B. salt of N-acyl derivatives of mono-carboxylic acid (e.g., acylglycinate, acylalanate), wherein greater than 65% of the acyl group (e.g., 65 to 100%, preferably 65 to 90%) has chain length $C_{14}$ or less; and
      C. mixtures thereof;
      wherein the surfactant of (i) comprises 65% or greater of triethanolamine or potassium salt or mixtures thereof of the amino acid surfactant;
    (ii) glycerol; and
    (iii) water;
      wherein the weight ratio of glycerol to water ranges from 3:1 to 1:3 in the aqueous phase, preferably 2:1 to 1:2.

Preferably, the volume average diameter of the oil droplets of the general nanoemulsion is 20 to 400 nanometers, more preferably 20 to 250. Preparation of nanoemulsion using specific counterions and ratios of glycerol to water are novel and provide ease of production.

In a different aspect of the invention, the invention provides droplets as small as 20 to 400 nm, preferably 20 to 250 nm volume average diameter wherein the nanoemulsion is prepared using a conventional rotor-stator mixer (based on high-speed rotation of the rotor blades, measured by revolutions per minute, or rpm). This avoids use of homogenizers which are based on high pressure. This in turn saves on energy and expensive equipment. Further, compositions prepared by this process are contemplated by the invention, It is noted that, if used as the only emulsifier in the aqueous phase, the sodium salt of mono- or di-carboxylic amino acid surfactants, such as sodium cocoyl glycinate (mono-carboxylic amino acid surfactant) and sodium lauroyl glutamate(di-carboxylic amino acid surfactant), tends to yield larger droplet (greater than 400 nm). As noted, sodium counterions may comprise up to 35% of all counterions for amino acid surfactants.

The weight ratio of glycerol over water ranging from 3:1 to 1:3 in the external aqueous phase, together with fatty acid and use of at least 65% (e.g., 65% to 100%) select salts of acyl amino acid surfactant allow formation of oil droplets as small as 20 to 400 nm when using only rotor-stator mixer (allowing savings in energy and cost).

The claims are intended to cover the salts of N-acyl derivatives of amino acids, for example, whether formed by us or bought as a prepared surfactant product (as would occur in the vast majority of all cases).

Preferably, nanoemulsions of the invention will typically have volume average diameter of droplets of 400 or less, preferably 350 or less, for example, 300 or less, or 20 to 300; or 20 to 250; or 20 to 200. Preferred emulsifier is potassium and/or alkanolamine salts of N-acyl derivatives amino acid surfactants. More preferably, only potassium amino acid surfactant is used. Regardless of the final droplet size, when two emulsions are prepared (for example, using rotor-stator high shear mixer at identical rotor speeds), the emulsion made with glycerol to water ratio of 3:1 to 1:3 (replacing water in otherwise identical nanoemulsion) has oil droplet size of $\frac{1}{6}$ to $\frac{1}{3}$ the size of droplets in the emulsion made when no glycerol is used. Glycerol to water ratio of 2:1 to 1:2 is preferred.

In previous applications, applicants have prepared nanoemulsions in a two-step process by first mixing the oil phase and the aqueous phase using a conventional rotor-stator mixer or other type of high shear devices, and then using a homogenizer, preferably at a process pressure of 7000 pounds per square inch (psi) or less, preferably 6000 psi or less; most preferably 5000 psi or less. Applicants previously found that, using $C_8$ to $C_{18}$ fatty acid as co-emulsifier in the oil phase, significantly reduces droplet size. In the subject invention, applicants have found that combination of fatty acid in oil phase; and glycerol to water levels of 3:1 to 1:3 allows not only preparation of droplets of size 20 nm to 400 nm in a single step, but allows preparation of drops of size 20 to 400, preferably 20 to 250 nm using rotor-stator device such that no high pressure homogenizer device is required. Thus, not only is there a one-step process, but costs of energy consumed operating the high pressure homogenizer and of the homogenizer device are avoided.

Preferably greater than 65% of chain length of N-acyl chains on the amino acid based surfactants used in the present invention are $C_{14}$ or less. Such preferred nanoemulsion composition, once formed, provides several advantages. For example, the nanoemulsion composition can be readily incorporated into personal cleanser compositions, either liquid cleansers or bar soaps. Further, the predominantly shorter chain N-acyl groups (relative to longer chain $C_{16}$ and $C_{18}$, for example) on the surfactant enable good lather formation in the cleanser compositions.

Thus, the novel nanoemulsions are sensorially pleasing (e.g., due to unexpectedly small droplet size), provide efficient oil deposition, provide superior stability (again because of smaller droplet size), and are ideally suited (because of preferred surfactant chain length selection) for use in personal cleansing liquids while providing excellent lather.

Moreover, because glycerol is used in place of water, there is lowered water activity, e.g., from 0.96 to as low as 0.6. This level water activity is within the ranges to inhibit bacteria growth, and potentially allows use of only fungicide or even no preservatives in nanoemulsions either as an intermediate raw material or as a final product.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

In one aspect, the present invention provides novel nanoemulsions containing a specific selection of oils, surfactants (having minimum required amounts of specific counterions) and specific ratio of glycerin to water. Applicants have surprisingly found that nanoemulsions of droplet size 20 to 400 nm can be prepared in a one-step process. In one embodiment, nanoemulsions of droplet size 20 to 400 nm, preferably 20 to 250 nm can be made in one-step using only a conventional rotor-stator mixer. Use of expensive and high energy homogenizer devices, operated in the high pressure range (1500 to 5000 psi), such as used in EP Application No. 16166487.5 relating to nanoemulsion with fatty acid, is thus avoided. Even in the broader composition aspect (with droplet size as small as 20 to 400 nm), it is the use of specific counterions and glycerol to water ratios which permits easier one-step processing. Both novel nanoemulsions which permit easier production of 20 to 400 nm droplets and the process of using only rotor-stator mixer (while still permitting production of droplets of size 20 to 400 nm) are claimed.

The novel nanoemulsions are ideally suited for use in soap bars or liquid cleansing compositions, for example, structured (e.g., micellar or lamellar structured) liquid cleansing compositions.

The N-acyl derivatives of amino acid surfactants (e.g., acylglutamate, acylaspartate, acylglycinate, acylalanate surfactants) of this invention preferably have greater than 65%, preferably greater than 75%, preferably greater than 80% of $C_{14}$ or shorter acyl chain (preferably they have greater than 75% acyl chain which are $C_{12}$, $C_{14}$ and mixtures thereof). The chosen surfactants provide multiple advantages when final nanoemulsions are mixed into fully formulated soap bars or liquid personal cleansing compositions. First, the amino acid surfactants used are known to be less irritating than harsher surfactants typically used such as sodium lauryl sulphate and sodium lauryl ether sulphate (SLES). Also, as noted, the chain length is selected so the surfactants are suitable for use in structured personal cleansing liquids while providing minimal interference with such structuring. Further, the selected predominantly shorter chain lengths ensure the surfactants will provide good foam.

In one co-pending application (EP Application No. 16166486.7), applicants claim similar nanoemulsions which comprise N-acyl derivatives of di-carboxylic acids and which are not specifically directed to those containing fatty acid emulsifier. In this co-pending application, small size droplets are obtained using high pressure (e.g. 5000 psi) homogenizer devices; and multiple passes are needed for petrolatum droplets of less than 200 nanometers (volume average diameter) to be made. Our formulations permit rotor-stator devices (less energy and cheaper) to be used to make nanoemulsions with droplet size as small as 20 to 250 nm and which can be prepared in one-step. It is thus far more convenient and offer great cost savings.

In a second co-pending application (EP Application No. 16166487.5), unexpectedly applicants found that using fatty acid as co-emulsifier yielded significantly smaller droplets, and that these smaller droplet nanoemulsions were obtained more efficiently using high pressure homogenization (e.g., single pass). Furthermore, using fatty acid as co-emulsifier permitted use of N-acyl derivatives of amino acid surfactants which are in liquid format, contain high amount of inorganic salts and have pH as high as 10 (which were not used in the first co-pending case). The co-emulsifier permits production of small droplets whether the amino acid surfactants are derivatives of dicarboxylic or mono-carboxylic amino acids. In the present application, applicants have found a way to obtain all the advantages of nanoemulsions having fatty acid as noted (e.g., using industrial liquid amino acid surfactant); and the further advantage (using glycerol in aqueous phase at defined ratios) of providing droplets as small as 20 to 400 nm, preferably 20 to 200 nm, and wherein this can be done using a rotor-stator device. As indicated, this provides cost savings on energy and investment on equipment, removing a barrier of mass production of nanoemulsions in the cosmetic industry. It is, as indicated a one-step process.

In short, use of glycerol in defined ratios with water (in aqueous phase) in combination with fatty acids and select amino acid surfactants having at least certain levels of defined counterions permits small droplet nanoemulsions to be obtained even more efficiently (without using high capital cost and high energy consuming high pressure homogenization process.). Even further, because glycerol is used in place of water, there is lowered water activity. This level water activity is within the ranges to inhibit bacteria growth, and potentially allows use of only fungicide or even no preservatives in nanoemulsions either as an intermediate raw material or as a final product.

In general, small size droplets help provide more efficient deposition in cleansing compositions. For example, cationic polymers typically used in fully formulated liquid cleanser more readily deposit the smaller droplets than larger droplets onto skin. Large oil droplets require stabilizers to suspend the large oil droplets. The small size oil droplets from the nanoemulsion, when incorporated into a cleansing liquid, also provide greater stability. Smaller droplets are also viewed as more aesthetically pleasing.

The nanoemulsions of the invention are defined with more particularity below.

Oil Phase

Oils in the oil phase of the nanoemulsions may be triglyceride oil or oils (animal and/or vegetable oils); petrolatum; or mixtures of one or more triglyceride oil with petrolatum.

Examples of triglyceride oils which may be used include soybean oil, sunflower seed oil, coconut oil, rapeseed oil, palm oil, palm kernel oil, grape seed oil, shea butter, cocoa butter and fish oil. Soybean and sunflower seed oils are preferred triglycerides.

The oil in the oil phase may also be petrolatum. The petrolatum preferably has a melting point ranging from 30° to about 60° C. Examples of such petrolatum jellys include Vaseline® Petrolatum Jelly from Unilever, WHITE PETROLATUM USP from Calumet Penreco, Petrolatum G2212 and White Protopet® 1S from Sonneborn.

Also suitable are the vegetable oils gelled with beeswax or vegetable wax. Examples of such gelled vegetable oils include NaturalAtum from Koster Keunen, Inc. and Unpetroleum Jelly from Camden-Grey Essential Oils, Inc.

The oils can range from 40% to 75% by wt., preferably 50% to 65% by wt. of the total nanoemulsion composition. The preferred volume average diameter of the triglyceride oil or petrolatum droplets is 20 to 400 nm, preferably 20 to 300nm, more preferably 20 to 250 nm, or 20 to 200 nm. Lower level can be 20 or 30 or 40 or 50; upper level can be 300 or 250 or 200 or 175 or 150. In one aspect of the invention, oil droplets of size 20 to 400, preferably 20 to 250, or 20 to 200 are formed by a process in which conventional rotor-stator device is utilized (high pressure homogenizer device is avoided).

The choice of triglyceride oils and petrolatum helps impart emolliency and occlusivity to skin when the triglyceride oils and/or petrolatum deposit onto skin after the skin is washed with fully formulated cleansing compositions into which the nanoemulsions of this invention have been incorporated.

In addition to the triglyceride oil (or oils) and/or petrolatum, the oil phase may comprise oil soluble skin beneficial actives such as, for example, Vitamin A, Vitamin E, sun screen, fragrances, retinol palmitate, 12-hydroxy stearic acid, conjugated linoleic acid; antibacterial agents; mosquito repellents etc. at level of 0.01 to 5%.

Another ingredient which might be found in the oil phase is an oil phase stabilizer. For example, small amounts (0.01 to 2%, preferably 0.1-1% by wt. nanoemulsion) of antioxidant may be used. When the oil used is triglyceride, a preferred antioxidant which may be used is butylated hydroxytoluene (BHT). This is often used as a food grade antioxidant.

In addition to oils, the oil phase contains $C_8$ to $C_{18}$, preferably $C_{10}$ to $C_{14}$ fatty acids in an amount ranging from 1.5 to 10% by wt. total nanoemulsion. More specifically, the ratio of fatty acid and oil ranges from 1:40 to 1:6. Examples of fatty acid which may be used include lauric acid, myristic acid, palmitic acid, stearic acid, coconut fatty acid and mixtures thereof. Preferably, lauric acid is used. The fatty acid is used as a co-emulsifier.

Aqueous Phase

The aqueous phase contain salts of N-acyl derivatives of amino acids (e.g., di- or mono-carboxylic acid) as primary emulsifier. Preferred di-carboxylic amino acid emulsifiers are acylglutamate and acylaspartate surfactants. Preferred mono-carboxylic amino acid emulsifiers are acylglycinate and acylalanate. Preferably, these are triethanolamine and potassium salts of N-acyl derivatives of amino acids, wherein greater than 65% of the acyl chains have chain length $C_{14}$ or less, e.g., $C_8$ to $C_{14}$ (e.g., derived from coconut fatty acid). The acyl chains preferably have greater than 75%, more preferably greater than 80% C14 or less chain length. Preferably, greater than 75%, most preferably greater than 80% of the chain length are $C_{12}$, $C_{14}$ or mixtures thereof. These predominantly short chain acyl groups (relative to longer chain $C_{18}$ and $C_{18}$, for example) ensure that, when nanoemulsions of the invention are incorporated into fully formulated liquid cleansing compositions (especially structured liquid cleansing compositions), they help maintain or enhance foaming capacity.

There are typically two formats of amino acid surfactants commercially available. One is powder or flake format, which is typically more expensive and high in purity. Examples of solid dicarboxylic amino acid surfactants include:
  potassium N-cocoacyl_I-Glutamate (e.g., Amisoft® CK-11 by Ajinomoto)
  potassium N-myristoyl-L-glutamate (Amisoft® MK-11 by Ajinomoto)
  potassium N-lauroyl-L-glutamate (Amisoft® LK-11 by Ajinomoto).

Sodium glutamates (e.g., sodium N-cocoyl-L-glutamate such as Amisoft® CS-11 from Ajinomoto) may be used, but must be used at levels of 35% or less of total amino acid salts.

Examples of solid monocarboxylic amino acids surfactants include:
  potassium cocoyl glycinate (e.g., Amilite® GCK-11 by Ajinomoto)

Liquid amino acid surfactants typically contains 20 to 35% surfactant active, high in pH and inorganic salt (e.g. from 3 to 6% KCl). Examples include:
  AMISOFT® CK-22: Potassium Cocoyl Glutamate (30% Aqueous Solution)
  AMISOFT® LT-12: TEA-Lauroyl Glutamate (30% Aqueous Solution)
  AMISOFT® CT-12 TEA-Cocoyl Glutamate (30% Aqueous Solution)
  AMILITE® ACT-12: TEA-Cocoyl Alaninate (30% Aqueous Solution)
  AMILITE® GCK-12/GCK-12K: Potassium Cocoyl Glycinate(30% Aqueous Solution)
  Aminosurfact™ ACDP-L: Potassium Cocoyl Glutamate (22%)+Sodium Cocoyl Glutamate(7%)
  Aminosurfact™ ACMT-L: TEA-Cocoyl Glutamate(30% Aqueous Solution)

Again, sodium glutamate salts can be used, but can be used of levels of 35% maximum.

In addition to the Amisoft® and Amilite® series from Ajinomoto, Aminosurfact™ from Asahi Kasei Chemical Corporation), other suppliers of liquid amino acid surfactants include Solvay (e.g., Gerapon® PCG Potassium Cocoyl Glutamate aqueous solution), Galaxy (Galsoft® KCGL Potassium Cocoyl Glutamate aqueous solution) and Sino Lion (Eversoft® USK-30K Potassium Cocoyl Glutamate aqueous solution).

Triethanolamine or potassium salt of amino acid surfactants or mixtures thereof are the most preferred in this invention and they can be used as the only surfactant in the aqueous phase. The sodium salt of mono-carboxylic amino acid surfactant, such as sodium cocoyl glycinate, or sodium salt of di-carboxylic amino acid surfactant, e.g. sodium lauroyl glutamate, tends to yield larger droplet (greater than 400 nm), as shown in Comparisons A and E, compared with potassium salts, under similar processing conditions in this invention. Optionally, the sodium salt of mono-carboxylic amino acid surfactant, or sodium salt of di-carboxylic amino acid surfactant, may be used in this application when in combination with triethanolamine or potassium salt of amino acid surfactants at a level less than 35% of the sodium salt of all amino acid surfactants (as percent active).

Furthermore, liquid form of amino acid surfactant is preferred, which is cost effective and convenient to use. Liquid amino acid surfactants typically contains 20 to 35% surfactant active, high in pH and inorganic salt (e.g. up to 6% or higher KCl or NaCl).

Optionally, other mild anionic or amphoteric cleansing surfactants may be used in the aqueous phase. Anionic surfactants which may be used include sodium cocoyl isethionate, sodium cocoyl methyl isethionate, sodium trideceth sulphate, sodium lauryl ether sulfate-3EO, and other amino acid based surfactants, such as sodium lauroyl sarcosinate, sodium cocoyl sarcosinate and sodium methyl cocoyl taurate. Amphoterics such as coco betaine, cocamidopropyl betaine, sodium lauroamphoacetate, lauramidopropyl hydroxysultaine and cocamidopropyl hydroxysultaine can also be used. These co-surfactants are typically present at a level of less than 35%, preferably less than 25%, more preferably less than 15% of total surfactants in the aqueous phase.

Overall surfactants in aqueous phase comprise 2 to 12% preferably 3 to 10% by wt. of total nanoemulsion. As indicated, triethanolamine or potassium salts of N-acyl derivatives of amino acid, preferably acylglutamate, acylaspartate, acylglycinate, acylalaninate or mixtures thereof are the principal surfactant of the nanoemulsion. They constitute 65% or greater, preferably 70% or greater of all surfactant in the aqueous phase. Preferably they constitute greater than 80%, more preferably greater than 90%. They may of course be the only surfactant present in the aqueous phase.

Also included in the aqueous phase is glycerol, widely used as humectant in cosmetic applications. Preferably, the weight ratio of glycerol and water present in aqueous phase ranges from 3:1 to 1:3, more preferably, 2:1 to 1:2.

A critical distinction between previous application in which fatty acids were incorporated into nanoemulsion (in oil phase) and the present invention is that the aqueous phase of the subject invention further comprises glycerol with the weight ratio of glycerol and water ranging from 3:1 to 1:3. Preferably 2:1 to 1:2. Lower level of glycerol may be 8 or 9 or 10 or 11 or 12 or 13% by wt. Upper level may be 40 or 25 or 24 or 23 or 22 or 21 or 20% by wt. but amount of water falls within the defined ratios. Thus, if 9% glycerol is used, the level of water in the aqueous phase may range between 3% and 27% by wt. In general, glycerol may be present at levels ranging from 8 to 40% of total nanoemulsion. The inclusion of glycerol reduces the water level and binds water present in aqueous phase thus resulting in low water activity ($a_w$). Water activity indicates the amount of free water within a cosmetic composition and is determined by comparing the vapor pressure of the composition containing water with the vapor pressure of pure water. AquaLab Water Activity Meter from Decagon is one of devices for such measurement. Reduced water activity is used in cosmetic and food industries to inhibit the growth of microorganisms. In the present invention, water activity is reduced from 0.96 (without glycerol) to as low as 0.68 (with glycerol). This range of water activity is within the ranges where bacteria growth is inhibited even without use of additional bactericide. Thus, this potentially allows use of only fungicide or even self-preservation (no bactericide or fungicide) in nanoemulsions either as an intermediate raw material or as a final product.

Preparation of nanoemulsions

Both aqueous and oil phases are heated up to 75 C or until the oil phase is melted in separate containers. The melted oil phase is gradually added to aqueous phase with agitation, followed by intensive mixing by a conventional rotor/stator device until the desired droplet size is reached.

Surprisingly, and unexpectedly, it has been found that specific combination of (1) glycerol in the aqueous phase (in defined ratio to water), with (2) select salts of amino acid based surfactant (e.g., certain counterions forming 65% or more of all counterion on the surfactant) as well as (3) fatty acid as co-emulsifier, permit production of oil droplets of size 20 to 400 nm. In one embodiment, droplets may have size of 20 to 400 nm and are made by a process using conventional rotor-stator mixers. Typically, the mixer operates at rotor speed up to 7000 RPM (or rotor tip speed of 7 to 25 meter per second depending on the size of the rotor), i.e., without high energy consuming high pressure homogenization. Preferably, the rotor speed is 3000 to 7000 rpm. Oil droplets produced without glycerol are 3 to 6 times as large as those with glycerol produced using the same conventional rotor-stator high shear devices.

Conventional rotor/stator mixers typically consist of a rotor rotating at high speed inside a close fitting stator. Widely used conventional rotor/stator high shear devices in cosmetic industry, such as Silverson® high shear in-line or in-tank mixer, are suitable for this application in large scale commercial production.

In the examples, the following terms are determined as noted below:

The volume average diameters, D[4,3], are determined by a Malvern Mastersizer. The water activity, $a_w$, is measured at 26° C. by AquaLab Water Activity Meter from Decagon.

EXAMPLES 1-3 AND COMPARATIVES A-B

Emulsions were prepared in a one liter ESCO mixer equipped with a rotor/stator high shear device (ESCO-LABOR AG, Switzerland). The aqueous phase, including liquid surfactant, glycerol, water, preservative were added to the ESCO mixer, mixed to uniformity and heated up to about 55 to about 75° C. The oil phase was combined and heated up to about 55 to about 75° C. or until melted in a separate container, gradually added to the aqueous phase in the ESCO mixer under agitation and was intensively mixed by the rotor/stator device. When the addition of all oil phase was completed, the mixture in the ESCO mixer was further intensively mixed by the rotor/stator device at either 3000 RPM or 7000 RPM (rotor speed) for up to 5 minutes. The mixture was then cooled and discharged. The oil droplet size was measured by a Malvern Mastersizer. The water activity, $a_w$, is measured at 26° C. by AquaLab Water Activity Meter from Decagon.

| Ingredient | Example 1 Wt. % | Comp. A Wt. % | Example 2 Wt % | Comp. B Wt. % | Comp. C Wt % | Comp. D Wt % | Example 3 Wt. % |
|---|---|---|---|---|---|---|---|
| Oil Phase | | | | | | | |
| Ultimate 76 Coconut oil (Cargill) | — | — | — | — | — | — | 60 |
| Soybean Oil | — | 55 | — | — | — | — | — |
| Petrolatum G2212 | 55 | — | 60 | 60 | 60 | 60 | — |
| Lauric acid | 4 | 4 | 4.36 | 4.36 | 1.09 | 1.09 | 3.96 |
| BHT Food Grade | — | 0.4 | — | — | — | — | 0.4 |
| Aqueous Phase | | | | | | | |
| Potassium Cocoyl Glutamate (Galaxy, Galsoft KCGL, Active 30%) | 20 (6*) | — | 20 (6*) | 20 (6*) | 23.27 (7*) | 23.27 (7*) | 20 (6*) |
| Sodium Lauroyl Glutamate (AMISOFT® LS-11) | — | 6 | — | — | — | — | — |
| Deionized Water | 9.6 | 23.2 | 0 | 15.24 | 0 | 15.24 | 0 |
| Glycerin | 11 | 11 | 15.64 | 0 | 15.64 | 0 | 15.64 |
| Preservative | 0.4 | 0.4 | — | 0.4 | — | 0.4 | — |
| D[4,3] nm@3000 rpm | 697 | 3516 | 367 | 1646 | — | — | 515 |
| D[4,3] nm@7000 rpm | 319 | 445 | 148 | 473 | 466 | 2587 | 159 |
| pH | 6.81 | 5.62 | 6.49 | 6.94 | 7.89 | 7.94 | 6.84 |
| Water activity, $a_w$ | 0.852 | — | 0.678 | 0.961 | 0.662 | 0.958 | 0.669 |

*number in parentheses indicates active level

Examples 1-3 with 6% potassium cocoyl glutamate (active level) as primary emulsifier, 4.0 to 4.4% fatty acid as co-emulsifier and glycerol level ranging from 11 to 15.64%, yield final oil droplets ranging from 148 nm to 319 nm (at 7000 rpm), and water activity ranging from 0.669 to 0.852.

In comparison A, sodium lauroyl glutamate was primary emulsifier (at levels exceeding 35% of total counterion), resulting in a droplet size larger than 400 nm (at 7000 rpm).

The only difference between Example 2 and Comparison B is that the former contains glycerol and the later does not contain glycerol. The droplet sizes of Comparison B are 3.2 (at 7000 rpm) or 4.5 (at 3000 rpm) times of those of Example 2 respectively. It is seen that glycerol is critical to producing small droplet size. The water activity in Example 2 is 0.678, significantly lower than 0.961 of Comparison B.

Comparison C shows that lower fatty acid level yield oil droplet larger than 400 nm (at 7000 rpm). Comparison D yields even larger oil droplets when fatty acid level is low and no glycerol is present, which demonstrates the importance of the levels of fatty acid and glycerol in low energy rotor/stator production of nanoemulsions.

EXAMPLE 4 AND COMPARATIVE E

Examples 4 and Comparative E were prepared similarly as Examples 1-3.

| Ingredient | Example 4 Wt % | Comparison E Wt % |
|---|---|---|
| Oil Phase | | |
| Petrolatum G2212 | 60 | — |
| White petrolatum | — | 60 |
| Lauric acid | 4.36 | 4.36 |
| Aqueous Phase | | |
| Potassium cocoyl glycinate (Amilite GCK-12K, active 30%) | 20 (6*) | — |
| Sodium Cocoyl Glycinate (Galsoft, Active 20%) | — | 20 (4*) |
| Glycerin | 15.64 | 15.64 |
| $D_{[4,3]}$ nm@3000 rpm | 452 | — |
| $D_{[4,3]}$ nm@7000 rpm | 143 | 929 |
| pH | 6.51 | 6.23 |
| Water activity | 0.74 | 0.746 |

*number in parentheses indicates active level

Potassium salt of mono-carboxylic amino acid surfactant, Potassium cocoyl glycinate, is used in Example 4, yielding a droplet size of 143 nm at 7000 RPM, similar to that of Example 2, where potassium salt of di-carboxylic amino acid surfactant is used.

The sodium salt of mono-carboxylic amino acid surfactant, such as sodium cocoyl glycinate, tends to yield larger droplet (greater than 400 nm), as shown in Comparison E.

EXAMPLE 5. MOISTURIZING CLEANSER

| Ingredient | Wt % |
|---|---|
| Nanoemulsion from Example 2 | 93.8 |
| MACKAM ™50-UL (37%, Cocamidopropyl Betaine) | 4 (1.5 active) |
| Jaguar ® C-13S | 0.2 |
| Fragrance, other additives | 2 |

Small amount of other surfactant, cationic polymer and fragrance can be post-added into nanoemulsion made in Example 2, yield a moisturizing cleanser with good lather.

The invention claimed is:

1. A nanoemulsion composition comprising:
   a) an internal phase comprising (1) 40 to 75% by wt. of total nanoemulsion composition of oils selected from the group consisting of triglyceride, petrolatum and mixtures thereof, wherein the melting point of the petrolatum is 30 to 60° C.; and (2) 1.5 to 10% by wt. nanoemulsion of a $C_8$ to $C_{18}$ fatty acid; and
   b) an external aqueous phase comprising:
      i. 2 to 12% by wt. as active of total nanoemulsion composition of a surfactant or surfactants which are N-acyl derivatives of amino acid salt; wherein the surfactant of (i) comprises 65% or greater of trialkanolamine or potassium salts or mixtures thereof of said surfactant;
      ii. glycerol, and
      iii. water
   wherein the weight ratio of glycerol to water in aqueous phase is 3:1 to 1:3; and
   wherein the volume average diameter of droplets of (a) is 20 to 400 nanometers.

2. The nanoemulsion composition according to claim 1, wherein said surfactant or surfactants are selected from the group consisting of
   i. salt of N-acyl derivatives of dicarboxylic amino acid, wherein greater than 65% to 100% of the acyl group has chain length of $C_{14}$ or less; and
   ii. salt of N-acyl derivatives of monocarboxylic amino acid, wherein greater than 65% of the acyl group to 100% of the acyl group has chain length $C_{14}$ or less; and
   iii. mixtures thereof.

3. The nanoemulsion composition according to claim 2, wherein the salt of N-acyl derivative of dicarboxylic amino acid is a salt of acylglutamic acid, salt of acylaspartic acid or mixture thereof.

4. The nanoemulsion composition according to claim 2, wherein the salt of N-acyl derivative of monocarboxylic amino acid is a salt of acylglycine, salt of acylalanine or mixture thereof.

5. The nanoemulsion composition according to claim 1, wherein volume average diameter of the droplets is 20 to 250 nm.

6. The nanoemulsion composition according to claim 1, where the oil is a triglyceride oil and said triglyceride oil is selected from the group consisting of soybean oil, sunflower seed oil, coconut oil, rapeseed oil, palm oil, palm kernel oil, grape seed oil, fish oil and mixtures thereof.

7. The nanoemulsion composition according to claim 1, where the oil is petrolatum and the melting point of the petrolatum is 30 to 60° C.

8. The nanoemulsion composition according to claim 1, where the oil is an oil mixture comprising triglyceride oil and petrolatum.

9. The nanoemulsion composition according to claim 1, wherein said fatty acid having a chain length $C_8$-$C_{18}$ is selected from the group consisting of lauric acid, myristic acid, palmitic acid, stearic acid, coconut fatty acid and mixtures thereof.

10. The nanoemulsion composition according to claim 9, wherein the fatty acid is present at a level of 2 to 7% by wt.

11. The nanoemulsion composition according to claim 1, wherein the nanoemulsion is prepared using conventional rotor/stator high shear devices.

12. The nanoemulsion composition according to claim 1, wherein the nanoemulsion is prepared in the absence of high pressure homogenization.

13. The nanoemulsion composition according to claim 11, wherein the rotor speed of said conventional rotor/stator is 3000 to 7000 RPM.

14. The nanoemulsion composition according to claim 1, wherein the surfactant of (b), prior to formation of the nanoemulsion, is a powder or liquid surfactant.

* * * * *